United States Patent [19]

Janitschke et al.

[11] Patent Number: 4,517,382
[45] Date of Patent: May 14, 1985

[54] 1-FORMYL-TRI- AND TETRAMETHYL-CYCLOHEX-1-EN-3-ONE OXIMES

[75] Inventors: Lothar Janitschke, Kleinniedesheim; Werner Hoffmann, Neuhofen, both of Fed. Rep. of Germany

[73] Assignee: BASF Aktiengesellschaft, Ludwigshafen, Fed. Rep. of Germany

[21] Appl. No.: 418,605

[22] Filed: Sep. 16, 1982

[30] Foreign Application Priority Data

Sep. 23, 1981 [DE] Fed. Rep. of Germany ....... 3137802

[51] Int. Cl.$^3$ ............................................. C07C 131/10
[52] U.S. Cl. .................................................... 564/267
[58] Field of Search ................ 564/253, 267; 568/378

[56] References Cited

U.S. PATENT DOCUMENTS 3,293,301 12/1966 Derfer et al. ...................... 568/338

FOREIGN PATENT DOCUMENTS 2724180 12/1977 Fed. Rep. of Germany .

OTHER PUBLICATIONS

Pepperman, Armand B. *J. Org. Chem.* vol. 46, (1981), pp. 5039-5041.

Ter-Sarkisyan, G. S. et al. *Chemical Abstracts* vol. 68, (1968) #104,589u.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

1-Formyl-2,6,6-trimethyl-cyclohex-1-ene derivatives of the formula I

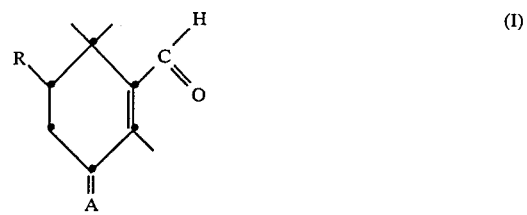

where R is —H or —$CH_3$ and A is O or NOH are prepared by nitrosylating the corresponding 1-formyl-2,6,6-trimethyl-cyclohex-1-ene or -cyclohex-2-ene and, where appropriate, hydrolyzing the resulting oxime (where A is NOH) to the corresponding ketone (where A is O).

The compounds I, except where R is H and A is O, are novel.

2 Claims, No Drawings

1-FORMYL-TRI- AND TETRAMETHYL-CYCLOHEX-1-EN-3-ONE OXIMES

The present invention relates to a novel process for the preparation of 1-formyl-2,6,6-trimethyl-cyclohex-1-ene derivatives of the general formula I

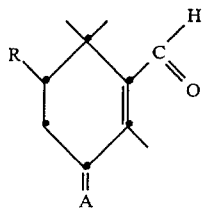

where R is —H or —CH₃ and A is oxygen or an oxime group.

The invention also relates to the compounds I as novel compounds, with the exception of 1-formyl-2,6,6-trimethyl-cyclohex-1-ene (Ia).

Compound Ia, which corresponds to formula I with R=—H and A=oxygen, is disclosed in German Laid-Open Application DOS No. 2,724,180 to be a valuable flavoring for foodstuffs, drinks, pharmaceutical preparations and tobacco.

As is also disclosed by the said DOS, Ia has hitherto only been obtainable by very involved methods.

Thus, this compound can be prepared in a five-stage synthesis, wherein 1-formyl-2,6,6-trimethyl-hex-2-ene (IIb) is first brominated to the corresponding 2,3-dibromo compound, HBr is eliminated therefrom to give the corresponding 3-bromo-cyclohex-2-ene, the bromine is replaced by the acetate radical, the acetate is hydrolyzed and the resulting 1-formyl-2,6,6-trimethyl-cyclohex-1-en-3-ol is oxidized with manganese dioxide to give Ia. An alternative version of this process, via 1-hydroxymethyl-2,6,6-trimethyl-cyclohex-1-en-3-ol, is also rather unsatisfactory.

Moreover, German Laid-Open Application DOS No. 2,724,180 refers to a prior art synthesis of Ia, wherein the thio compound

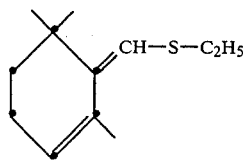

is used as a starting material and converted to Ia in a plurality of stages, including 2-brominations.

The oxidation of 1-formyl-2,6,6-trimethyl-cyclohex-1-ene (IIa) with selenium dioxide, according to J. Org. Chem. USSR, English edition, 4 (1968), 308–312, is also not a useful method for the industrial production of Ia, since the yields achieved are only about 20% and the use of selenium dioxide, which is very toxic, presents problems.

It is an object of the present invention to provide a more economical method of preparing Ia and its 5-methyl-homolog.

Since, moreover, compounds containing the 2,6,6-trimethyl-cyclohexane structural unit are of great importance in carotinoid chemistry and in the chemistry of fragrances and aromas, it is a further object of the invention to increase the synthesis possibilities in these fields by providing novel intermediates.

We have found that these objects are achieved by a novel process for the preparation of the 1-formyl-2,6,6-trimethyl-cyclohex-1-ene derivatives defined at the outset, wherein (a) a 1-formyl-2,6,6'-trimethyl-cyclohex-1-ene (IIa) and/or -cyclohex-2-ene (IIb)

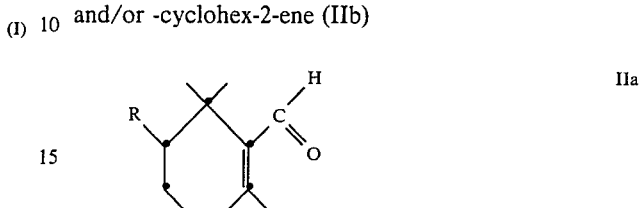

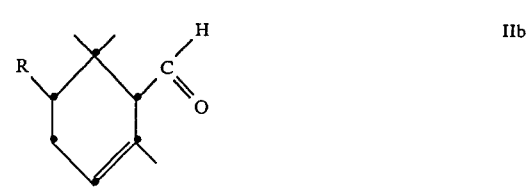

is reacted, at from −10° C. to 45° C., with a nitroso compound of the general formula III

which is capable of decomposing under the reaction conditions into an anion X⊖ and the nitrosyl cation [NO]⊕, and (b) the resulting oximes Ib and Ib' (I with A=NOH)

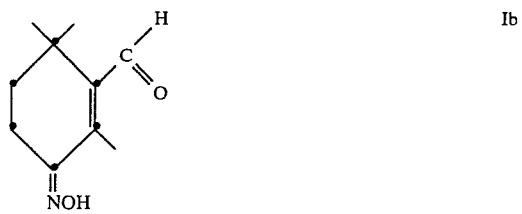

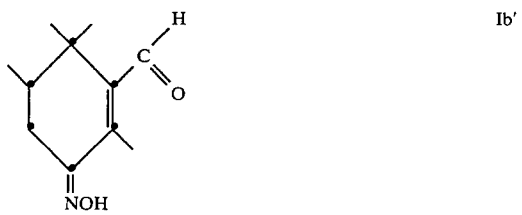

are hydrolyzed in a conventional manner to give Ia and Ia' (I, with A=O)

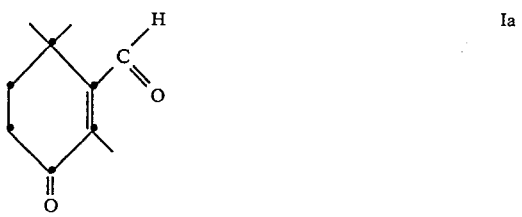

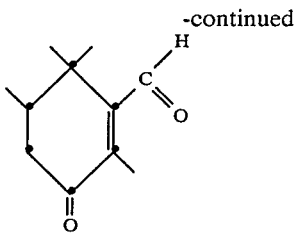

Novel valuable intermediates which we claim are 1-formyl-2,6,6-trimethyl-3-oximido-cyclohex-1-ene, 1-formyl-2,5,6,6-tetramethyl-3-oximido-cyclohex-1-ene and 1-formyl-2,5,6,6-tetramethyl-cyclohex-1-en-3-one.

The starting compounds IIa and IIb, which can also be employed in the form of a mixture, are known and may be obtained, for example, by the process described in Can. J. Chem. 49 (1971), 1764–1766.

To ensure complete reaction of IIa or IIb, the nitrosylating agent is employed in at least equimolar amount, and advantageously in an excess of up to 0.5, preferably up to 0.3 and especially 0.1, mole per mole of IIa or IIb. A greater excess of nitrosylating agent leads to increased formation of by-products.

The reaction may actually take place with the isomer IIb. Since the isomer IIa should be in equilibrium with IIb under the reaction conditions, IIb would constantly be replenished.

On this assumption, the reaction could be regarded as an addition reaction of X—NO at the double bond in the 2,3-position. In that case, an aldehyde with a nitroso group in the 3-position and the radical X in the 2-position would be formed as an intermediate. The oxime Ib would then be arrived at by, for example, elimination of $X^\ominus$ to give the unsaturated nitroso compound, and subsequent acid rearrangement of the latter.

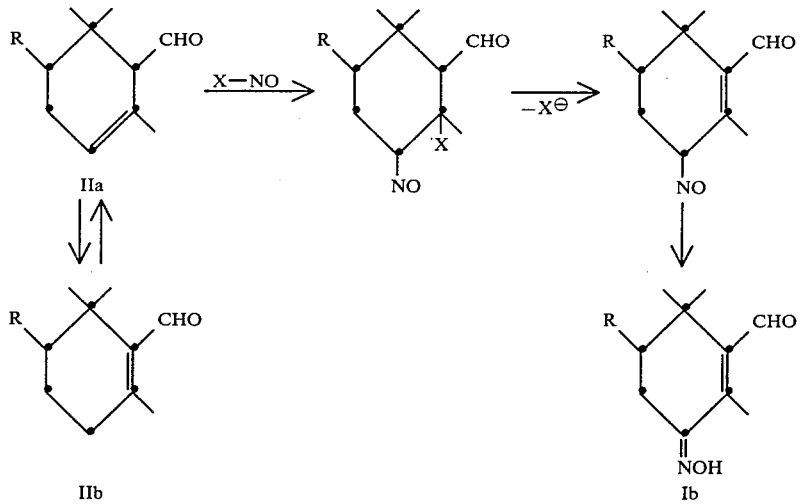

The essential feature of the process according to the invention is the oximation of IIa or IIb with the nitroso compound III, a reaction which contrary to expectations takes place smoothly, to give a single product, without, say, addition of the two molecular fragments X and NO of III to the double bond of IIa or IIb.

Since, according to our observations to date, the only feature required of the nitrosylating agent III is that it should be capable of forming a nitrosyl cation and an anion $X^\ominus$ under the reaction conditions, the remainder of the chemical nature of III is of minor importance and at most influences the reaction rate and the yield. However, the choice of nitrosylating agent depends not only on these aspects but also on the overall economics of the process, which are in every instance better than in the case of the conventional syntheses.

Suitable nitrosylating agents, which exhibit polarity of the following type:

$$X^{\sigma-}-NO^{\sigma+}$$

are, for example, nitrosyl halides, eg. nitrosyl chloride, as well as nitrosylsulfuric acid and alkyl nitrites of the formula IIIa $$R'-O-NO \qquad (IIIa)$$

where R' is $C_1$-$C_8$-alkyl.

An acid is required for the rearrangement of the NO adduct, first formed, to the oximes Ib and Ib', and for liberation of the reactive species from nitrosylating agents such as the alkyl nitrites.

Accordingly, it is advisable to carry out the reaction in the presence of a strong mineral acid, such as hydrochloric acid or sulfuric acid. If an alkyl nitrite in an aliphatic alcohol is used, it is advantageous to employ alcoholic hydrochloric acid ranging in strength from 2% to a saturated solution.

Nitrosylsulfuric acid is advantageously employed in commercial quality (about 45% strength in sulfuric acid). The acids are in general employed in amounts of from 1.5 to 35 moles per mole of III.

It is moreover advantageous to carry out the reaction in a homogeneous phase in the presence of a solvent, such as a lower aliphatic alcohol or liquid $SO_2$. The use of methanol or ethanol is particularly advantageous. The amount of solvent is preferably from 2 to 40 kg, especially from 2.5 to 5 kg, per kg of IIa or IIb.

The nitrosylation reaction temperature is in general from $-10°$ C. to 45° C., preferably from 10° to 30° C., and in particular room temperature.

If the reaction is carried out batchwise, the procedure followed is in general to take an acid solution of IIa or IIb and to add gradually thereto the nitrosylating agent or a solution thereof. If the reaction is carried out continuously, on the other hand, it is advantageous to pass the reactants or their solutions, in a constant ratio, simultaneously through the reactor.

The reaction mixture can be worked up in a conventional manner, by first distilling off the volatile constituents, taking up the residue in a water-insoluble solvent, such as diethyl ether, and adding aqueous sodium hydroxide solution to the mixture. However, the reaction mixture can also be worked up with water alone instead of with aqueous sodium hydroxide solution, by concentrating the reaction mixture, adding a water-insoluble solvent and then pouring the batch onto a mixture of about 4.3 kg of ice and about 4.3 kg of water per kg of IIa or IIb employed. The organic phase is then separated off and freed from solvent. The product, which in most cases is first formed as an oil, can be purified by crystallization, for example from cyclohexane.

The further conversion—which is generally virtually quantitative—of the oximes Ib or Ib' to the ketones Ia or Ia' is then effected in a conventional manner by oxime cleavage methods, for example by heating with an aqueous alcoholic NaHSO$_3$ solution or with an aqueous mineral acid. The ketones can then be isolated analogously to the oximes or by steam distillation.

The oximes Ib and Ib', which are obtained in yields of from 40 to more than 90%, are valuable intermediates for organic syntheses, for example for the preparation of the corresponding ketones Ia and Ia' and of a number of known scents and aromas.

The ketone Ia, which can be obtained from Ib in 43–58% yield of pure product, is a known aroma and moreover an important intermediate for the preparation of carotenoids and of scents and aromas.

Similar remarks as to usefulness as an intermediate apply to the novel compound Ia'. This compound per se is also a valuable scent and aroma, having a fruity fragrance note.

EXAMPLE 1

Preparation of 1-formyl-2,6,6-trimethyl-3-oximido-cyclohex-1-ene (Ib)

152 g (1 mole) of a mixture of equal parts of 1-formyl-2,6,6-trimethyl-cyclohex-1-ene and -cyclohex-2-ene are added to a mixture of 1,000 ml of methanol and 40 ml of concentrated sulfuric acid at 20°–25° C., the batch is then stirred for 1 hour at room temperature, 323 g (1.2 moles) of a 43–45% strength solution of nitrosylsulfuric acid in sulfuric acid are then added dropwise at 20°–25° C. and thereafter the batch is stirred for a further hour at the reaction temperature.

The methanol is distilled off at a bath temperature of 30° C. under 26 mbar, the residue is taken up in 2,000 ml of diethyl ether and the solution is poured onto a mixture of 3,000 g of ice and 480 g of 50% strength by weight sodium hydroxide solution. The ether phase is separated off and the aqueous phase is extracted with 4 times 500 ml of diethyl ether.

Conventional working up for the combined ether phases gives 176 g of crude oxime (97% of theory) in the form of an oil. The pure oxime is obtained from this, by crystallization from 1,000 ml of cyclohexane, in the form of crystals of melting point 96°–100° C., the yield being 69%. According to thin layer chromatography, the oily residue also consists predominantly of 1-formyl-2,6,6-trimethyl-3-oximido-cyclohex-1-ene.

The identity of the compound is proved in the conventional manner by various physical methods:

| IR spectrum (KBr tablet): | |
|---|---|
| 3260 cm$^{-1}$ | OH |
| 1643 cm$^{-1}$ | C=O |
| 1568 cm$^{-1}$ | C=C |
| $^1$H-NMR (CDCl$_3$/220 MHz)$\delta$: | |
| 10.33 ppm, s, 1H, CHO | |
| 10.04 ppm, sbr., 1H, OH | |
| 2.70 ppm, t (J~7.5 Hz), 2H, CH$_2$—4 | |
| 2.24 ppm, s, 3H, CH$_3$ on C—2 | |
| 1.60 ppm, t (J~7.5 Hz), 2H, CH$_2$—5 | |
| 1.25 ppm, s 6H, CH$_3$ on C—6 | |
| $^{13}$C-NMR (CDCl$_3$/20.12 MHz)$\delta$: | |
| 193.52 ppm | CHO |
| 157.67 ppm | C-3 |
| 146.24 ppm | C-2 |
| 141.66 ppm | C-1 |
| 36.52 ppm | C-5 |
| 33.53 ppm | C-6 |
| 26.89 ppm | 2CH$_3$ on C-6 |
| 19.29 ppm | C-4 |
| 11.81 ppm | CH$_3$ on C-2 |

Elementary analysis: Calculated: C 66.3%, H 8.3%, O 17.7%, N 7.7%. Found: C 66.3%, H8.2%, O 18.0%, N 7.9%.

EXAMPLE 2

Preparation of Ib 7.6 g (50 millimoles) of 1-formyl-2,6,6-trimethyl-cyclohex-1-ene are added dropwise, at 0°–5° C., to 100 ml of a saturated solution of HCl in ethanol, the resulting mixture is stirred for a further hour at 0°–5° C., and 5.85 g (60 millimoles) of n-pentyl nitrite are then added dropwise at 0°–5° C. The resulting reaction mixture is stirred for a further hour at 0°–5° C. and is then worked up by a method similar to Example 1, to give the oxime. The yield of pure crystalline Ib is 66% of theory; further amounts of Ib are contained in the mother liquor from the crystallization. They can either be isolated therefrom, or be reacted further.

A similar result (yield of pure substance: 44.2% of theory) is achieved if 1-formyl-2,6,6-trimethyl-cyclohex-2-ene is used as the starting compound.

EXAMPLE 3

7.6 g (50 millimoles) of 1-formyl-2,6,6-trimethyl-cyclohex-1-ene are added dropwise, at 0°–5° C., to a mixture of 100 ml of ethanol and 2 ml of concentrated sulfuric acid, the resulting mixture is stirred for a further hour at 0°–5° C. and thereafter 14.7 g of an about 43–45% strength solution of nitrosylsulfuric acid in sulfuric acid are added dropwise at 0°–5° C. The resulting reaction mixture is stirred for a further hour at 0°–5° C. and is then worked up by a method similar to Example 1, to give the oxime. 6.3 g of crude product (69.6% of theory) result. After crystallization from 63 ml of cyclohexane, 5.1 g of chromatographically pure product (56.4% of theory) are obtained.

EXAMPLE 4

Preparation of 1-formyl-2,5,6,6-tetramethyl-3-oximido-cyclo-hex-1-ene (Ib')

This compound is prepared similarly to Example 1, starting from a mixture of equal parts of 1-formyl-2,5,6,6-tetramethyl-cyclohex-1-ene and -cyclohex-2-ene and 296 g of an about 43–45% strength solution of nitrosylsulfuric acid in sulfuric acid; the crude yield is 72%, and the yield of pure crystalline product, of melting point 88°–91° C., is 36%.

Physical data of the pure compound:

| IR (KBr tablet): | |
|---|---|
| 3600–2700 cm$^{-1}$ | OH |
| 1675 cm$^{-1}$ | C=O |
| 1585 cm$^{-1}$ | C=C |
| $^1$H-NMR (CDCl$_3$/80 MHz)δ: | |
| 10.29 ppm, s, 1H, | CHO |
| 2.20 ppm, s, 3H, | CH$_3$ on C-2 |
| 1.73 ppm, m, 1H, | CH$_5$ |
| 1.25 ppm, s, 3H, | CH$_3$ on C-6 |
| 1.14 ppm, s, 3H, | |
| 0.98 ppm, d (J~7 Hz), 3H, CH$_3$ on C-5 | |
| $^{13}$NMR (CDCl$_3$/90.52 MHz)δ: | |
| 194.18 ppm | CHO |
| 157.27 ppm | C-3 |
| 146.52 ppm | C-2 |
| 140.32 ppm | C-1 |
| 37.10 ppm | C-5 |
| 36.81 ppm | C-6 |
| 27.22 ppm | C-4 |
| 25.80 ppm | CH$_3$ on C-6 |
| 20.93 ppm | |
| 15.53 ppm | CH$_3$ on C-5 |
| 11.78 ppm | CH$_3$ on C2 |

Elementary analysis: Calculated: C 67.7%, H 8.8%, O 16.4%. N 7.2%. Found: C 67.9%, H 8.6%, O 16.7%, N 7.2%.

Mass spectrum: 195 m/e M⊕; 178 m/e M⊕−17 (—OH); 166 m/e M⊕−29 (—CHO).

EXAMPLE 5

Preparation of 1-formyl-2,6,6-trimethyl-cyclohex-1-en-3-one (Ia)

45.2 g (0.25 mole) of the oxime Ib, 300 ml of ethanol and 300 ml of a 40% strength aqueous NaHSO$_3$ solution are boiled under reflux for 3 hours. Conventional working up of the reaction mixture by neutralization and extraction with ether gives the ketone Ia in a yield of pure product of 57% of theory.

Physical data:

| boiling point = 54–57° C./0.01 mbar; | |
|---|---|
| IR (film) | |
| 1680 cm$^{-1}$ | C=O |
| 1665 cm$^{-1}$ | |
| 1585 cm$^{-1}$ | C=C |
| $^1$H-NMR (CDCl$_3$/80 MHz): | |
| 10.37 ppm, s, 1H | CHO |
| 2.57 ppm, t (J~7 Hz), 2H, CH$_2$—4 | |
| 2.05 ppm, s, 3H, CH$_3$ on C-2 | |
| 1.87 ppm, t (J~7 Hz), 2H, CH$_2$—5 | |
| 1.34 ppm, s, 6H | CH$_3$ on C-6 |
| $^{13}$C-NMR (CDCl$_3$/90.52 MHz)δ: | |
| 200.39 ppm | C-3 |
| 195.65 ppm | CHO |
| 153.83 ppm | C-1 |
| 140.35 ppm C-2 | C-2 |
| 37.73 ppm | C-5 |
| 34.38 ppm | C-4 |
| 34.25 ppm | C-6 |
| 26.74 ppm | 2CH$_3$ on C-6 |
| 10.35 ppm | CH$_3$ on C-2 |

Mass spectrum: 166 m/e M⊕; 151 m/e M⊕−15 (—CH$_3$); 137 m/e M⊕−29 (—CHO).

Fragrance note: fruity, herbal, lemon-like.

Hydrolysis of the oxime by means of dilute sulfuric acid, with simultaneous removal of the ketone by steam distillation, and subsequent fractionation gives the ketone Ia in a yield of pure product of 43% of theory.

EXAMPLE 6

Preparation of 1-formyl-2,5,6,6-tetramethyl-cyclohex-1-en-3-one (Ia')

The preparation is carried out similarly to Example 5. 30 g (0.15 mole) of 1-formyl-2,5,6,6-tetramethyl-3-oximido-cyclohex-1-ene, 190 ml of ethanol and 190 ml of a 40% strength aqueous NaHSO$_3$ solution are employed.

Working-up is effected with 204 ml of a 20% strength Na$_2$CO$_3$ solution. Extraction is carried out with 5 times 100 ml of ether.

Crude product: 24.4 g (90.4% of theory). The pure aldehyde can be obtained by distillation. Boiling point=63°–65° C./0.1 mbar.

| IR (film): | |
|---|---|
| 1683 cm$^{-1}$ | unsaturated carbonyl |
| 1667 cm$^{-1}$ | |
| 1600 cm$^{-1}$ | C=C |
| $^1$H-NMR (CDCl$_3$/80 MHz)δ: | |
| 10.30 ppm, s, 1H | CHO |
| 1.99 ppm, s, 3H, | CH$_3$ on C-2 |
| 1.29 ppm, s, 3H | CH$_3$ on C-6 |
| 1.23 ppm, s, 3 H | |
| 0.99 ppm, d (J~7 Hz), 3 H, CH$_3$ on C-5 | |
| $^{13}$C-NMR (CDCl$_3$/90.52 MHz)δ: | |
| 200.10 ppm | C-3 |
| 196.19 ppm | CHO |
| 154.70 ppm | C-1 |
| 138.84 ppm | C-2 |
| 42.14 ppm | C-4 |
| 38.92 ppm | C-5 |
| 37.69 ppm | C-6 |
| 20.50 ppm | CH$_3$ on C-6 |
| 20.22 ppm | |
| 15.32 ppm | CH$_3$ on C-5 |
| 10.30 ppm | CH$_3$ on C-2 |

Mass spectrum: 180 m/e M⊕; 165 m/e M⊕−15 (—CH$_3$); 151 m/e M⊕−29 (—CHO).

Fragrance note: fruity.

We claim:
1. 1-Formyl-2,6,6-trimethyl-3-oximido-cyclohex-1-ene.
2. 1-Formyl-2,5,6,6-tetramethyl-3-oximido-cyclohex-1-ene.

* * * * *